United States Patent [19]

Wong

[11] Patent Number: 5,164,305

[45] Date of Patent: Nov. 17, 1992

[54] STREPTOMYCES PROMOTER AND METHOD OF USE THEREOF

[75] Inventor: Hing C. Wong, San Ramon, Calif.

[73] Assignee: Cetus Oncology Corporation, Emeryville, Calif.

[21] Appl. No.: 466,981

[22] Filed: Jan. 18, 1990

[51] Int. Cl.$^5$ .............. C12P 21/00; C12N 15/00; C12N 15/76; C12N 1/20

[52] U.S. Cl. .............. 435/69.1; 435/172.1; 435/172.3; 435/252.35; 435/320.1; 536/27; 935/41; 935/43

[58] Field of Search ............ 536/27; 435/31, 69.1, 435/71.1, 71.3, 252.35; 935/41, 39

[56] References Cited

U.S. PATENT DOCUMENTS 4,865,982  9/1989  Burnett et al. .............. 935/41

OTHER PUBLICATIONS

Travers et al. (1983), Cell, vol. 35, pp. 265-273.
Valle et al. (1986), Gene, vol. 50, pp. 119-122.
Tommassen et al. (1987), J. Mol. Biol., vol. 198, pp. 633-641.
Wen et al. (1989), J. Biol. Chem., vol. 264, pp. 10996-11003.
Tsou et al. (1989), Biochem., vol. 28, pp. 969-975.
Warburton et al. (1983), Nucleic Acid Res., vol. 11, pp. 5837-5854.
Bibb et al., 1985, *Mol. Gen. Genet.* 199:26-36.
Murakami et al., Mar. 1989, *J. Bacteriology* 171(3):1459-1466.

*Primary Examiner*—Richard A. Schwartz
*Assistant Examiner*—Richard M. Lebovitz
*Attorney, Agent, or Firm*—Philip L. McGarrigle; Karen B. Dow

[57] ABSTRACT

A DNA sequence is described, which is a promoter for *Streptomyces*. This promoter is stronger than the wild type and ultimately increases transcription initiation and protein expression. Typically, a nucleotide base, such as guanine, is inserted into the promoter sequence between positions $-50$ and $-75$ to increase transcription initiation or protein expression. In a preferred embodiment, guanine is inserted between positions $-62$ and $-63$ of the promoter regulated by thiostrepton (tipA).

5 Claims, 4 Drawing Sheets

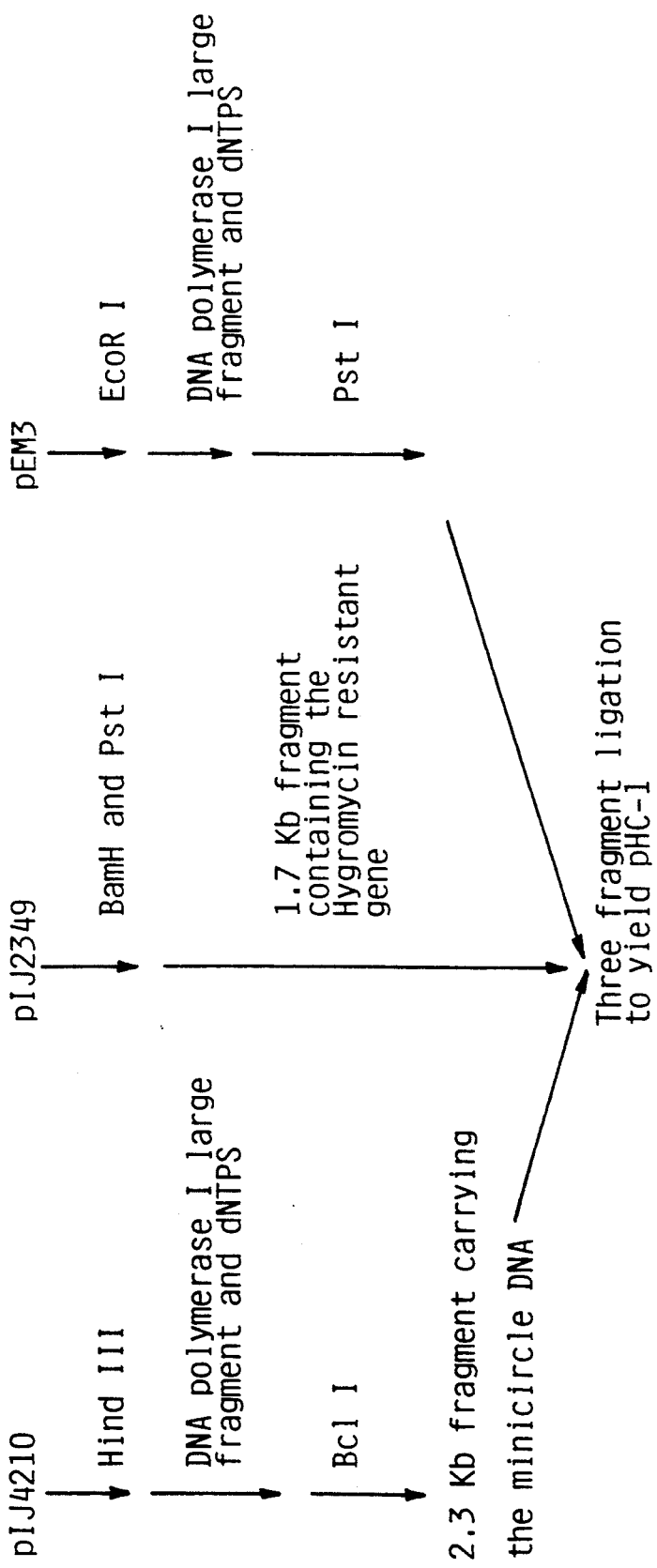

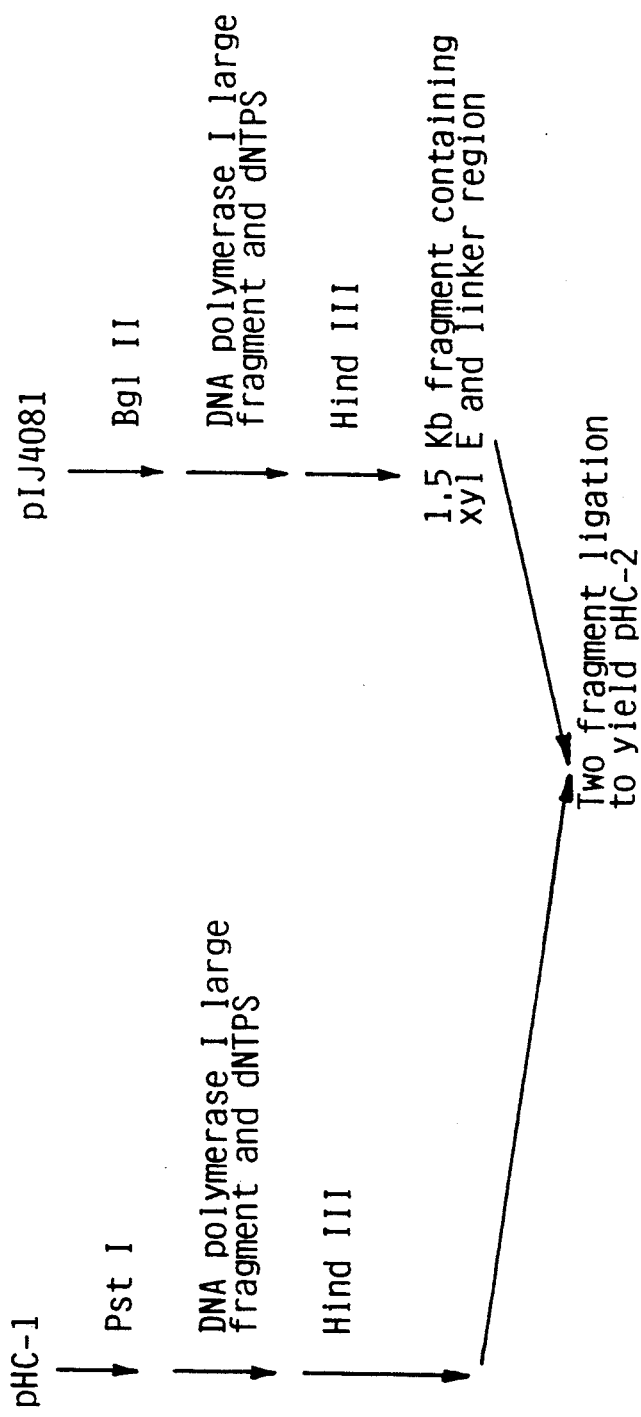

STREPTOMYCES PROMOTER AND METHOD OF USE THEREOF

FIELD OF THE INVENTION

The present invention relates to a Streptomyces promoter. More specifically, the present invention is an improved promoter which is useful to ultimately increase expression and efficiency of a gene.

BACKGROUND OF THE INVENTION

A promoter is a DNA sequence that promotes gene transcription to produce a messenger RNA and is recognized by RNA polymerase, which the promoter directs to the correct transcriptional start site. The *E. coli* promoter region, which is about 50 bases long, includes a common sequence (Pribnow box) of about 6 bases located upstream (in the 5' direction) from the site at which RNA synthesis begins. Five to eight bases separate the Pribnow box from the initiation site, so that it centers around the $-10$ position. Not all *E. coli* promoters have exactly the same sequence of bases in this region, but a sequence similar to TATAAT is typically found. Another consensus sequence, TTGACA, centers around $-35$; this region is also critical for the accurate and rapid initiation of transcription for most bacterial genes (see Darnell et al., 1986, *Molecular Cell Biology*, Scientific American Books Inc.). It has been noted that the $-10$ and $-35$ regions, as well as the spacing between them, are "major determinants of promoter strength." Because of the conserved regions, the RNA polymerase appears to make direct contact with the two regions. Consequently, "most mutations that affect promoter strength map to the strongly conserved bases in the $-10$ or $-35$ region or change the spacing between them" (Jansen, et al., 1985, Microbiology, Meetings for the American Society for Microbiology, American Society for Microbiology, Washington, D.C., pages 392-396 [1985]).

Mutations in the promoter may effect initiation. It has been shown that changes, deletions, or insertions in the promoter region may effect the way that RNA polymerase binds to the promoter. The ultimate result may be that more or less mRNA is produced. For example, Mandecki et al., 1982, *Nucleic Acid Research* 10:903-912, show that a two base pair insertion between the $-10$ and $-35$ regions lowered the promoter activity to 15% of the wild type; Post et al., 1978, *Cell* 15:231-236, show that a point mutation six bases upstream from the in vitro transcription site, which changed the Pribnow box, was important in the expression of an operon; and Youderian et al., 1982, *Cell* 30:843-853, show that specific decreases in the homology of a specific promoter with it consensus promoter sequence resulted in either a severe or a mild reduction in promoter activity (see Watson et al. *Molecular Biology of Gene* 4th edition Benjamin/Cummings Publishing Company, 1987). (Also see Botstein, 1972, *Virology* 49:268-282, and Siebenilist et al., 1980, *Cell* 20:269-281.)

Since promoters are known to effect ultimate gene expression, it would advantageous to increase the strength of promoter by manipulating the promoter sequence. That is the focus of the present invention, which is detailed and described more fully below.

SUMMARY OF THE INVENTION

The present invention is a DNA sequence comprising a Streptomyces promoter, wherein a base is inserted into the base sequence between positions $-50$ and $-75$, to increase transcription initiation. Preferably, the base insertion is made between $-60$ and $-65$, more preferably between positions $-62$ and $-63$. Preferably the base is guanine. Preferably, the DNA sequence is regulated by thiostrepton and is operable in Streptomyces. Preferably, the DNA sequence will hybridize to the following DNA sequence: GCGGCGGCTCACGGGCGTGGCA. More preferably, the DNA sequence is shown in FIG. 1. This improved DNA sequence may occur in the chromosome or may be in an expression vector. Preferably, the invention also includes a method for producing a protein using the DNA sequence detailed above.

The present inventor has made the surprising discovery that a base insertion between positions $-62$ and $-63$ of the Streptomyces thiostrepton promoter (tipA), increases promoter strength so that protein expression is increased 5-fold (while maintaining the regulatory aspects of the promoter). This is further surprising because the position of the mutation is outside the commonly recognized sequences for the promoter, i.e., near the $-10$ and $-35$ regions.

BRIEF DESCRIPTION OF DRAWINGS

FIG. 2 (2-1 and 2-2) is a diagram of the construction of pHC-1 and pHC-2. 2-1 illustrates the construction of pHC-1. 2-2 illustrates the construction of pHC-2.

DETAILED DESCRIPTION OF THE INVENTION

Figure 1:
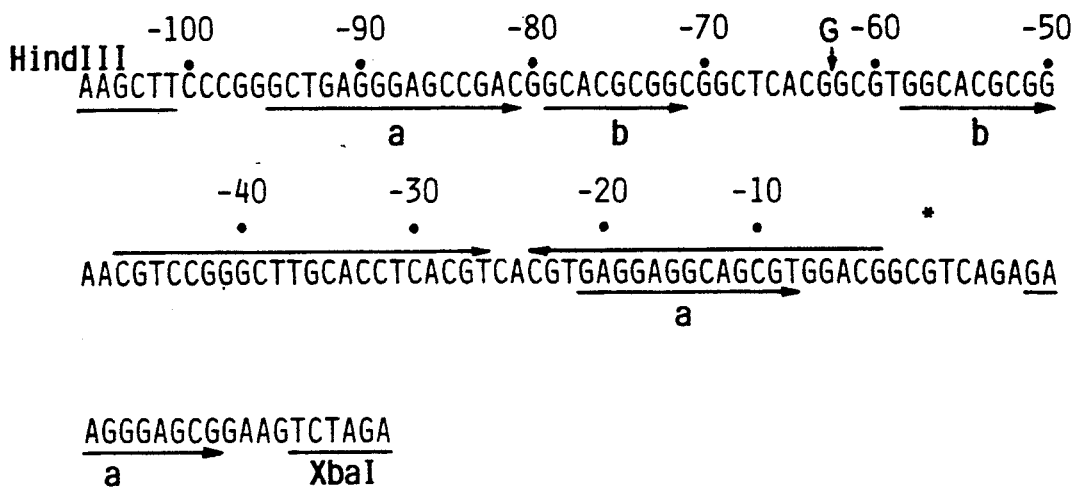
FIG. 1 is the DNA sequence of the tipA wild type and mutant promoters.
Figure 3:
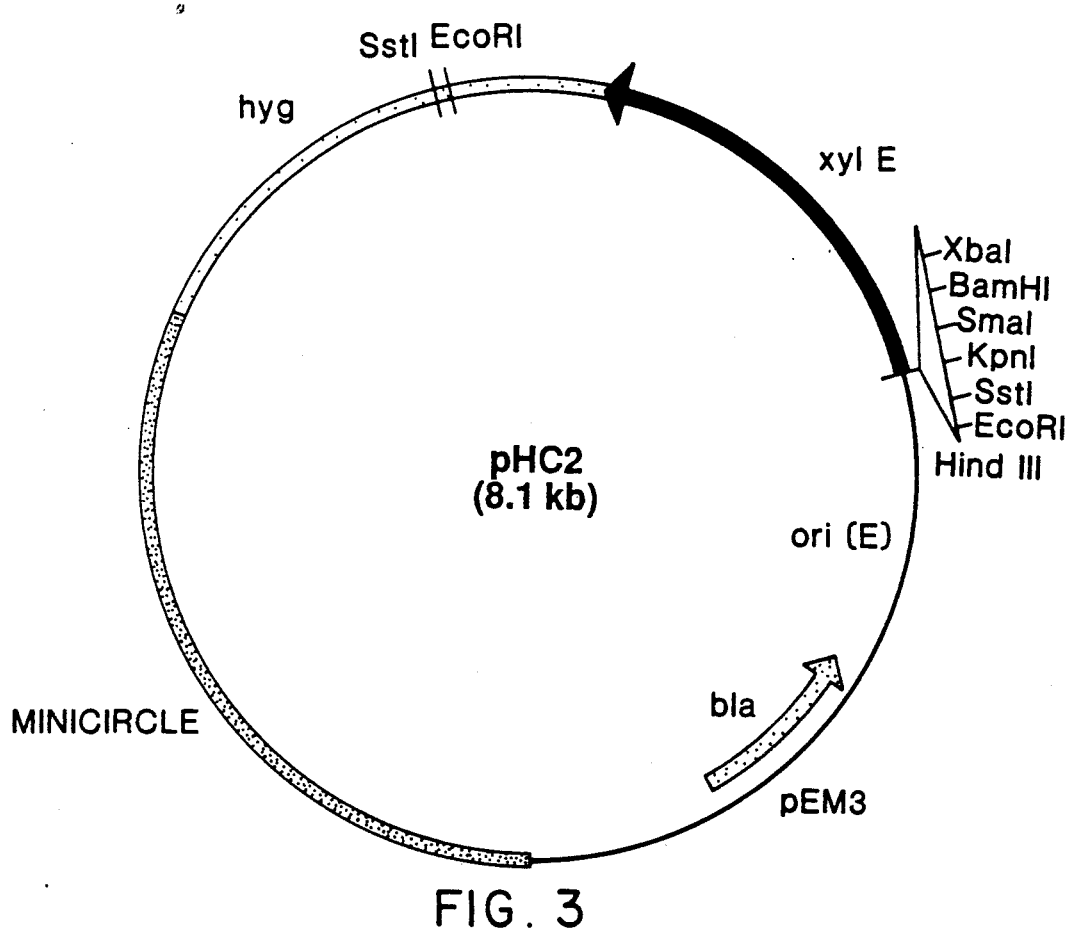
FIG. 3 is a circular map of pHC-2.

A promoter can be induced by a compound. In Streptomyces, thiostrepton is one such compound. Thiostrepton is a antibiotic which inhibits translation. However, it has been reported to induce a streptomyces promoter to express several proteins (Murakami et al., 1989, *Journal of Bacteriology* 171(3):1459-1466, which is hereby incorporated by reference in its entirety). Murakami et al. show that thiostrepton induces the expression of four proteins of unknown function in *Streptomyces lividans*. Murakami et al. note that the promoter that is induced (tipA) should be useful for expression studies in streptomycetes. Since the streptomycetes are commonly used to commercially produce antibiotics, the tipA promoter can prove commercially useful. For example, certain genes can be operably linked to the thiostrepton promoter to increase their expression. These may be naturally occurring streptomyces genes (for example, antibiotic producing genes) or heterologous genes (for example, mammalian genes such as interleukins, interferons, colony stimulating factors, tumor necrosis factor, etc.). (See, the two articles collected in *Microbiology*, 1985, American Society for Microbiology, Washington, D.C., pages 409-420, which are both hereby incorporated by reference in their entireties.) Preferably, the improved tipA promoter of the present invention is linked to a DNA sequence encoding a protein so that the protein may be controllably expressed. Preferably, other DNA control sequences are included that are necessary for production of the protein, such as ribosome binding sites, etc.

As stated above, the present invention is the discovery that inserting a guanine between positions $-62$ and $-63$ of the tipA promoter increases the strength of the promoter while maintaining the promoter control. This is an important discovery because this promoter may be useful to controllably overexpress various proteins made in streptomycetes. Currently, streptomycetes are used for pharmaceutical and antibiotic preparations. This invention may also be advantageous in further research into promoters.

Streptomyces are gram positive organisms with a complex cycle of morphological development. They can be grown from a spore on a solid surface to give rise to a branched septate substrate mycelium and aerial mycelium (see Hopwood et al., Regulation of Gene Expression-25 Years On, The 39th Symposium of the Society for General Microbiology, Cambridge University Press 1986, pages 251–276, which is hereby incorporated by reference in its entirety). However, in submerged culture, the cells do not sporulate. After they complete the vegetative state, they remain biologically active and can produce large amounts of secondary metabolites, such as antibiotics. To illustrate this point of the 4,973 natural antibiotics described by 1978, 2,769 were of streptomycetes origin. These antibiotics include aminoglycosides, macrolides, tetracyclines, polyethers, anasamycins, $\beta$-lactams, oligopeptides, etc. Streptomycetes can also produce other extracellular products, such as hydrolytic enzymes. See Chater et al., 1982, *Current Topics in Microbiology and Immunology* 96:69–95, which is hereby incorporated by reference in its entirety.

Although it is envisioned that the improved promoter can be inserted into all streptomycetes, exemplary hosts include the following: *Streptomyces lividans, S. coelicolor, S. griseus, S. parvulus, S. albus, S. vinaceus, S. acrimycinis, S. calvuligerus, S. limosus, S. rubiginosis, S. azureus, S. glaucenscens, S. rimosus, S. violaceotuber,* and *S. kanamyceticus.*

As stated above, an improved promoter is important because it can be linked to a gene of interest to increase the ultimate expression of that gene. The promoter can be operably linked to genes by means known in the art (see Maniatis et al., 1989, *Molecular Cloning: A Laboratory Manual*, Cold Spring Harbor Press, and U.S. Ser. No. 023,637, which are both herein incorporated by reference in their entireties). Generally speaking, restriction sites may be introduced into the promoter and a specific gene of interest so that the two may be joined. Thereafter, the promoter and gene may be introduced into a vector, which may or may not be able to integrate into the streptomyces chromosome. A mechanism for inserting the promoter and/or the gene into the chromosome may be by use of a DNA sequence which favors integration. An example of this DNA sequence is the mini-circle DNA which is described below and in Lydiate et al., 1986, *Mol. Gen. Genet.* 203:79–88, which is hereby incorporated by reference in its entirety.

The presently preferred tipA promoter differs from the wild type by one base. See FIG. 1 which compares the two sequences. The wild type promoter is the uninterrupted sequence, and the improved promoter is that sequence plus the guanine that is inserted between the bases at positions −62 and −63. There are also some other structures of interest. The sequences that are labeled with "a" and "b" are direct repeats. The "a" sequence is found at the positions −95 to −81, −20 to −8, and 6 to 15. The "b" sequence is shown at positions −79 to −72 and −58 to −50. There are also two inverted repeats, which occur at positions −48 to −26 and −2 to −22.

Even though the most preferred embodiment is shown in FIG. 1, other sequences may increase promoter strength and, therefore, transcription initiation. For example, other bases may be inserted in lieu of guanine, such as thymine, adenine, or cytosine. Also, the insertion may be made at points other than between −62 and −63. The insertion could occur somewhere between −60 and −65, or even between −50 and −75. Furthermore, increased initiation may occur if the sequence shown between −55 and −75 on FIG. 1 is shifted to a different position within the promoter. However, the shifted sequence should remain substantially homologous to the following sequence: GCGGCGGCTCACGGGCGTGGCA (the underlining denotes the inserted guanine).

The present invention will now be illustrated by reference to the following examples, which set forth the particularly advantageous embodiments. However, it should be noted that these embodiments are illustrative and are not to be construed as a restricting the invention in any way.

EXAMPLE 1

Construction of an Integrated Promoter-Probe Plasmid

The integrated promoter-probe plasmid was constructed to include the following components: an *E. coli* replication origin (colEI replication origin from the pUC18); an *E. coli* selectable marker (Tn3 $\beta$-lactamase); an indicator gene (catechol dioxygenase, designated XylE); a Streptomyces selectable marker (hygromycin resistance gene); a Streptomyces integration sequence (mini-circle DNA); and a linker region containing specific restriction sites (HindIII, KpnI, SmaI, BamHI, and XbaI). The general sequence for this plasmid's construction is shown in FIG. 2 and is recited below.

The plasmid pUC18 (commercially obtained) was partially digested with PvuII and then digested with EcoRI. The EcoRI restriction ends were repaired with DNA polymerases I fragment and four deoxyribonucleotide triphosphates. After the restriction ends were filled in, the plasmid was religated and transformed into *E. coli* DG101. Plasmids from ampicillin resistant transformants were isolated and analyzed. These plasmids were designated pEM3 (pUC18 without the lac promoter). Plasmid pEM3 was ligated with DNA sequences from the plasmids pIJ2349 (hygromycin resistance) and pIJ4210 (mini-circle DNA). Plasmids pIJ4210 and pIJ2349 were obtained from John Innes Institute, Norwich NR7UH, United Kingdom. Further information can be found in Chater et al., 1982, *Current Topics in Microbiology and Immunology* 96:69–95, for the pIJ101 series of plasmids and Hopwood et al., *Genetic Manipulation of Streptomyces,* a laboratory manual, The John Innes Foundation, Norwich, United Kingdom. The hygromycin resistance gene was obtained by digesting pIJ2349 to obtain a 1.0 kb fragment. The mini-circle DNA was obtained by digesting pIJ4210 to obtain a 2.10 kb fragment (see Lydiate et al. referred to above). After digestion with EcoRI and PstI, pEM3 was joined to the fragments from pIJ2349 and pIJ4210 in a three fragment ligation to yield pHC-I. Plasmid pIJ4081 was obtained from the John Innes Institute and was digested as shown in FIG. 2. After digestion with restriction enzymes, a 1.5 kb fragment containing the XylE and the linker region was obtained and ligated to the fragment generated from pHC-I, as also shown in FIG. 2. The resulting plasmid was designated pHC-2.

EXAMPLE 2

Cloning of the tipA Promoter

The tipA promoter was constructed using two overlapping oligonucleotides, a 77 and 78 base primer, as shown as follows:

77-mer

CCAAGCTTCC CGGGCTGAGG GAGCCGACGG CACGCGGCGG CTCACGGCGT GGCACGCGGA ACGTCCGGGC TTGCACC 78-mer CCTCTAGACT TCCGCTCCCT TCTCTGACGC CGTCCACGCT GCCTCCTCAC GTGACGTGAG GTGCAAGCCC GGACGTTC These two primers were annealed and extended by DNA polymerase I large fragment and deoxyribonucleotides. After extension, the double-stranded DNA was digested with HindIII and XbaI. The digested DNA was cloned into the HindIII-XbaI site of pUC18. The recombinant plasmid was sequenced. It contained the improved promoter having the guanine insertion between bases −62 and −63. The promoter was designated tipA-∇G62. The wild type and mutant promoters were subcloned into the promoter-probe plasmid pHC-2. The plasmid having the wild type promoter was designated pHC11-11, and the plasmid having the improved promoter was designated pHC11-3.

EXAMPLE 3 tipA Promoter Activity and *Streptomyces lividans*

Both plasmids were then transformed into *Streptomyces lividans*. Cultures of *Streptomyces lividans* were grown and the specific activity of the XylE gene was analyzed in the presence and absence of thiostrepton (thiostrepton induces the tipA promoter to transcribe the XylE gene). The results of this experiment are shown in Table I.

TABLE I

| tipA Promoter Activity in *Streptomyces lividans* | | | |
|---|---|---|---|
| | | Specific Activity of XylE* | |
| Construct | Promoter | −Thiostrepton | +Thiostrepton |
| pHC11-11 | tipA-wt | <0.5 | 36.3 |
| pHC11-3 | tipA-∇G62 | 12.0 | 182.2 |

*Specific activity is defined as mmoles of catechol semialdehyde formed per minute per mg of protein.

The results show that there was 5-fold more protein produced from the plasmid having the improved promoter.

The plasmid pHC11-3 has been deposited in Cetus' in-house depository as CMCC 3798 and in the ATCC as 40737.

The present invention has been described with reference to specific embodiments. However, this application is intended to cover those changes and substitutions which may be made by those skilled in art without departing from the spirit and the scope of the appended claims.

I claim:

1. A method for producing protein comprising operably linking a gene encoding the protein to the DNA sequence comprising a Streptomyces tipA promoter, wherein a guanine is inserted into the nucleotide base sequence of the promoter between positions −62 and −63, inserting the linked gene and DNA sequence into a cloning vehicle, transforming *Streptomyces lividans* with the cloning vehicle, cultivating the *Streptomyces lividans* and inducing the expression of the protein under suitable conditions, and collecting the expressed protein.

2. A DNA sequence comprising a Streptomyces tipA promoter, wherein a guanine is inserted into the nucleotide base sequence of the promoter between positions −62 and −63.

3. A DNA sequence in accordance with claim 2, wherein the DNA sequence is induced by thiostrepton.

4. A mutant DNA promoter sequence which has the nucleotide bases shown in FIG. 1, wherein a guanine is inserted into the sequence between positions −62 and −63.

5. A DNA sequence of claim 4, wherein the sequence is contained in a Streptomyces expression vector.

* * * * *